United States Patent
Kim et al.

(10) Patent No.: US 9,164,956 B2
(45) Date of Patent: Oct. 20, 2015

(54) VEHICLE CONTROL APPARATUS AND METHOD USING PRIVATE MEDICAL INFORMATION, AND MOBILE TERMINAL

(71) Applicant: Samsung Electronics Co., Ltd., Gyeonggi-do (KR)

(72) Inventors: Jun-Hyung Kim, Gyeonggi-do (KR); Young-Wan So, Gyeonggi-do (KR); Jong-Hyo Lee, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 0 days.

(21) Appl. No.: 13/781,036

(22) Filed: Feb. 28, 2013

(65) Prior Publication Data
US 2013/0226372 A1    Aug. 29, 2013

(30) Foreign Application Priority Data
Feb. 28, 2012    (KR) .................. 10-2012-0020320

(51) Int. Cl.
*G06F 17/00* (2006.01)
*G06F 19/00* (2011.01)
*B60W 50/00* (2006.01)

(52) U.S. Cl.
CPC .............. *G06F 17/00* (2013.01); *G06F 19/322* (2013.01); *G06F 19/3418* (2013.01); *B60W 2050/0064* (2013.01); *B60W 2050/0085* (2013.01); *B60W 2540/22* (2013.01)

(58) Field of Classification Search
CPC ... G06F 17/00; G06F 19/322; G06F 19/3418; G06F 19/3406; G07C 5/085; B60W 2540/22; B60W 2540/0064; B60W 2540/0085

USPC .................. 701/1, 2, 36; 370/331; 705/2, 3
See application file for complete search history.

(56) References Cited

U.S. PATENT DOCUMENTS

| | | | |
|---|---|---|---|
| 6,775,603 B2 | 8/2004 | Yester et al. | |
| 8,068,952 B2 | 11/2011 | Valentine et al. | |
| 8,311,702 B2 * | 11/2012 | Miki | 701/36 |
| 2004/0019416 A1 | 1/2004 | Chen et al. | |
| 2005/0107673 A1 * | 5/2005 | Ball | 600/301 |
| 2008/0215209 A1 | 9/2008 | Ikeda et al. | |
| 2010/0049068 A1 * | 2/2010 | Fuwamoto et al. | 600/509 |
| 2010/0161171 A1 * | 6/2010 | Valentine et al. | 701/33 |

(Continued)

FOREIGN PATENT DOCUMENTS

| | | |
|---|---|---|
| JP | 2004-058981 | 2/2004 |
| JP | 2008-213634 | 9/2008 |
| KR | 1020040018787 | 3/2004 |

OTHER PUBLICATIONS

European Search Report dated Jul. 3, 2015 issued in counterpart application No. 13754640.4-1952.

*Primary Examiner* — Marthe Marc-Coleman
(74) *Attorney, Agent, or Firm* — The Farrell Law Firm, P.C.

(57) ABSTRACT

A vehicle control apparatus and method using private medical information, and a mobile terminal are provided. An optimized driving environment is provided by searching controllable vehicle control nodes in a vehicle, upon reception of a driver's private medical information; determining if there is vehicle control information for controlling the searched vehicle control node; and controlling the vehicle control nodes using vehicle control information that corresponds to the received driver's private medical information if there is the vehicle control information for controlling the searched control nodes.

17 Claims, 10 Drawing Sheets

(56) References Cited

U.S. PATENT DOCUMENTS

| | | | |
|---|---|---|---|
| 2010/0185101 A1* | 7/2010 | Sakai et al. | 600/483 |
| 2011/0093136 A1 | 4/2011 | Moinzadeh et al. | |
| 2011/0210867 A1* | 9/2011 | Benedikt | 340/905 |
| 2012/0330173 A1* | 12/2012 | Park et al. | 600/521 |
| 2013/0009761 A1* | 1/2013 | Horseman | 340/425.5 |
| 2013/0054090 A1* | 2/2013 | Shin et al. | 701/36 |

* cited by examiner

VEHICLE CONTROL APPARATUS AND METHOD USING PRIVATE MEDICAL INFORMATION, AND MOBILE TERMINAL

PRIORITY

This application claims priority under 35 U.S.C. §119(a) to a Korean Patent Application filed in the Korean Intellectual Property Office on Feb. 28, 2012, and assigned Serial No. 10-2012-0020320, the entire disclosure of which is incorporated herein by reference.

BACKGROUND OF THE INVENTION

1. Field of the Invention

The present invention relates generally to a vehicle control apparatus and method, and more particularly, to a vehicle control apparatus and method and a related mobile terminal for offering optimized driving conditions by controlling the vehicle based on a driver's private medical information.

2. Description of the Related Art

Generally, vehicle control devices have been able to perform operations to offer the driver optimized conditions for driving, such as adjusting the driver's seat angle or adjusting the air conditioner.

Recently, a method has emerged for ensuring safe driving even if the driver gets into trouble due to the worsening of his/her health condition by enabling the driver to control driving conditions of the vehicle in response to his/her health condition.

Specifically, in such a method, the driver's medical information is stored in his/her mobile terminal, and when the driver gets in the vehicle with the mobile terminal, the mobile terminal is connected to a head unit for controlling operations of vehicle control nodes related to the vehicle's driving conditions, such as the rearview mirror, the air conditioner, the seat, etc. of the vehicle.

The driver's medical information is transferred from the mobile terminal to the head unit, and if it is determined from the driver's medical information that the driver is not in a proper condition to drive the vehicle, a warning phrase is displayed on a screen of the vehicle that the driver is not in the proper condition to drive the vehicle.

In other words, in the conventional method, information about the driver's medical condition stored in the driver's mobile terminal is transferred to the head unit of the vehicle and, if the driver's medical condition is not proper for driving, a warning phrase is displayed on the screen.

However, since the head unit simply presents an alarm to the driver, the driver may not clearly know of his/her health condition while driving.

Even after receiving the warning, it may be difficult or inconvenient for the driver, especially if the driver is a senior citizen or a disabled person, to manually establish and change operations of each of the vehicle control nodes to change the current driving condition. Furthermore, the driver may simply choose to ignore the warning.

In addition, if the driver manually controls operations of each of the vehicle control nodes while driving, the driver may possibly get into an accident due to the distraction.

SUMMARY OF THE INVENTION

The present invention has been made to address the problems and disadvantages described above, and to provide at least the advantages described below. Accordingly, an aspect of the present invention provides a vehicle control apparatus and method, and a related mobile terminal for automatically optimizing driving conditions of a vehicle for convenience and safety based on a driver's private medical information.

In accordance with an aspect of the present invention, a vehicle control apparatus using a driver's private medical information is provided. The apparatus includes a transceiver for transmitting and/or receiving information used to control a vehicle; a control node searcher for searching a controllable vehicle control node in the vehicle; a control node determiner for determining if there is vehicle control information for controlling the vehicle control node for adjustment of a driving condition; and a vehicle controller for controlling the control node determiner to determine if there is the vehicle control information for controlling the vehicle control node searched by the control node searcher, upon reception of the driver's private medical information; and controlling, if there is the vehicle control information for controlling the searched vehicle control node, the searched vehicle control node using vehicle control information that corresponds to the driver's private medical information.

In accordance with another aspect of the present invention, a mobile terminal for controlling a vehicle using a driver's private medical information is provided. The mobile terminal includes a transceiver for transmitting and/or receiving information used to control a vehicle; a terminal controller for obtaining the driver's private medical information for adjustment of a driving condition from a private medical information server having the driver's private medical information; obtaining a control nodes list of controllable vehicle control nodes in the vehicle from a head unit of the vehicle having the control nodes list; obtaining vehicle control information from a vehicle control information server having the vehicle control information predetermined to correspond to at least one piece of medical information; and controlling the vehicle control nodes using the vehicle control information for the obtained control nodes list in response to the obtained driver's private medical information.

In accordance with another aspect of the present invention, a vehicle control method of a vehicle control apparatus using a driver's private medical information is provided. The method includes searching for a controllable vehicle control node in a vehicle upon reception of the driver's private medical information; determining if there is vehicle control information for controlling the searched vehicle control node; and controlling, if there is the vehicle control information for controlling the searched vehicle control node, the searched vehicle control node using the vehicle control information that corresponds to the driver's private medical information.

In accordance with another aspect of the present invention, a method of controlling a vehicle using a driver's private medical information in a mobile terminal is provided. The method includes obtaining the driver's private medical information for adjustment of a driving condition from a private medical information server having the driver's private medical information; obtaining a control nodes list of controllable vehicle control nodes in the vehicle from a head unit of the vehicle having the control nodes list; obtaining vehicle control information from a vehicle control information server having the vehicle control information predetermined to correspond to at least one piece of medical information; and controlling the vehicle control nodes using the vehicle control information for the obtained control nodes list in response to the obtained driver's private medical information.

BRIEF DESCRIPTION OF THE DRAWINGS

The above and other aspects, features and advantages of the present invention will become more apparent by describing in detail exemplary embodiments thereof with reference to the attached drawings in which.

DETAILED DESCRIPTION OF EMBODIMENTS OF THE PRESENT INVENTION

Reference will now be made in detail to embodiments of the present invention, examples of which are illustrated in the accompanying drawings, wherein like reference numerals refer to the like elements throughout. Detailed description of well-known functionalities and configurations will be omitted to avoid unnecessarily obscuring the present invention.

The present invention automatically controls operations of vehicle control nodes controllable for driving conditions of a vehicle to optimize the driving conditions for the driver by offering the driver's private medical information from a mobile terminal to a head unit of the vehicle.

Figure 1:
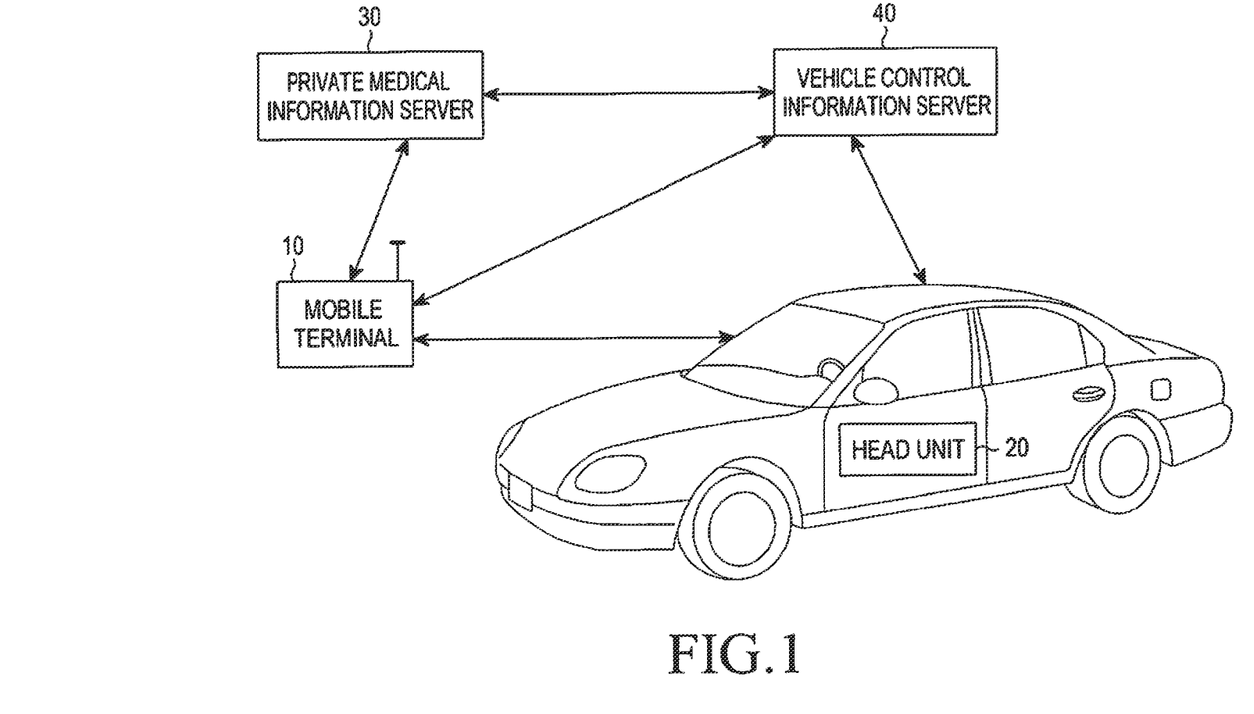
FIG. 1 is a schematic diagram of a vehicle control system using private medical information, according to an embodiment of the present invention.

FIG. 1 is a schematic diagram of a vehicle control system using private medical information, according to an embodiment of the present invention.

The vehicle control system includes a mobile terminal 10, a head unit 20, a private medical information server 30, and a vehicle control information server 40.

The mobile terminal 10 discovers the head unit 20 and establishes a connection with the head unit 20 after exchanging information for communication, such as IP addresses. The mobile terminal 10, upon request from the head device 20 for initiation of a service for offering an optimized vehicle driving condition for the driver, determines whether the mobile terminal has the driver's private medical information. When the mobile terminal 10 has the driver's private medical information, the mobile terminal 10 sends a request for a control nodes list of the controllable vehicle control nodes in the vehicle to the head unit 20. The control nodes list includes types of the controllable vehicle control nodes in the vehicle and associated control information.

When the mobile terminal 10 does not have the driver's private medical information, the mobile terminal 10 sends a request for the driver's private medical information to the private medical information server 30. Upon reception of the control nodes list, the mobile terminal 10 requests the vehicle control information server 40 for predetermined vehicle control information for controlling at least one vehicle control node in response to a plurality of pieces of medical information. Upon reception of the vehicle control information, the mobile terminal 10 identifies predetermined vehicle control information in response to the driver's private medical information, and generates a vehicle control command to control the vehicle control node in response to the identified vehicle control information. The mobile terminal 10 sends the vehicle control command to the head unit 20 to control the vehicle control node.

Furthermore, upon request from the head unit 20, the mobile terminal 10 requests the private medical information server 30 for the driver's private medical information and then forwards the driver's private medical information to the head unit 20.

The mobile terminal 10 send a request to the head unit 20 for the control nodes list, obtains the control nodes list in return, requests the private medical information server 30 for the driver's private medical information, and receives from the private medical information server 30 the vehicle control information in response to the requested driver's private medical information. The mobile terminal 10 selects from among pieces of vehicle control information some vehicle control information that corresponds to the control nodes list, and forwards the selected vehicle control information to the head unit 20.

The head unit 20 discovers the mobile terminal 10 and establishes a connection with the mobile terminal 10 after exchanging information for communication, such as IP addresses. The head unit 20 sends the mobile terminal 10 the control nodes list of vehicle control nodes at the request of the mobile terminal 10. Then, upon reception of a vehicle control command, the head unit 20 controls operations of at least one vehicle control node according to the vehicle control command.

Also, upon reception of the driver's private medical information, the head unit 20 sends a request to the vehicle control information server 40 for vehicle control information, obtains the vehicle control information in return, and controls operations of the vehicle control node using predetermined vehicle control information in response to the driver's private medical information.

The head unit 20, upon reception of the vehicle control information that corresponds to the control nodes list, controls the vehicle control node using the received vehicle control information.

The private medical information server 30 stores private medical information for at least one driver, and forwards the private medical information to the mobile terminal 10 or the vehicle control information server 40 upon request.

The vehicle control information server 40 stores vehicle control information predetermined to correspond to at least one driver, and forwards the vehicle control information to any of the mobile terminal 10, the head unit 20, and the private medical information server 30 upon request. In this regard, the vehicle control information server 40 detects vehicle control information predetermined to correspond to a particular driver's private medical information, and sends the vehicle control information to the head unit 20.

As such, the present invention offers the driver optimized driving conditions by automatically controlling a driving condition of the vehicle in response to the driver's private medical information.

Figure 2:
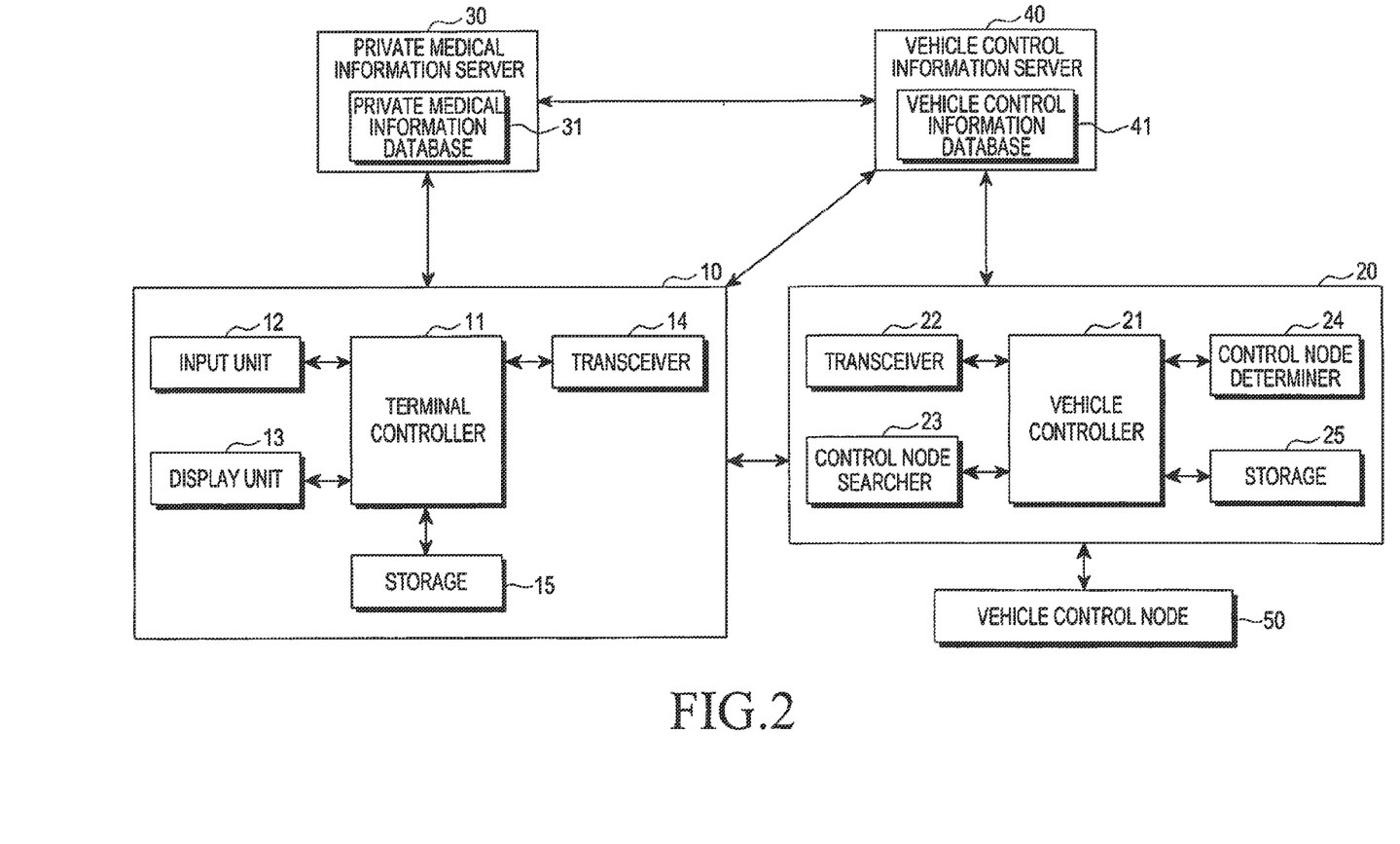
FIG. 2 is a schematic diagram of a mobile terminal, a head unit, a private medical information server, and a vehicle control information server, according to an embodiment of the present invention.

FIG. 2 is a schematic diagram of the mobile terminal 10, the head unit 20, the private medical information server 30, and the vehicle control information server 40, according to an embodiment of the present invention.

The mobile terminal 10 includes a terminal controller 11, an input unit 12, a display unit 13, a transceiver 14, and a storage 15.

The terminal controller 11 discovers the head unit 20, establishes a connection with the head unit 20, upon request for initiation of a vehicle driving condition offering service from the head unit 20, determines if the driver's private medical information (also referred to as the driver's personal health records) is stored in the storage 15, and sends a request for the driver's private medical information through the transceiver 14 if the driver's private medical information is not stored, or stored but does not have enough information to be used.

The terminal controller 11 sends a request for the control nodes list of controllable vehicle control nodes in the vehicle to the head unit 20 through the transceiver 14.

Upon reception of the control nodes list through the transceiver 14, the terminal controller 11 sends a request for vehicle control information predetermined to control at least one vehicle control node in response to pieces of medical information to the vehicle control information server 40 through the transceiver 14.

Upon reception of the vehicle control information through the transceiver 14, the terminal controller 11 identifies predetermined vehicle control information in response to the driver's private medical information, and generates a vehicle control command to control the vehicle control node in response to the identified vehicle control information.

The terminal controller 11 sends the generated vehicle control command to the head unit 20 through the transceiver 14.

The input unit 12 includes key buttons for entering key inputs, and delivers to the terminal controller 11 a key input signal that corresponds to each key input generated by the pressure of the key button. The display unit 13 displays output data generated in the mobile terminal 10.

The transceiver 14 sends a request for the driver's private medical information to the private medical information server 30, and receives the driver's private medical information from the private medical information server 30. This may be done in a secure manner, such as including a password or a personal identification number (PIN), or the like, and may require authentication and authorization for the transfer of such private information. The transceiver 14 also sends a request for vehicle control information to the vehicle control information server 40, and receives the vehicle control information from the vehicle control information server 40. The transceiver 14 sends a request for the control nodes list to the head unit 20, and receives the control nodes list from the head unit 20. The transceiver 14 sends a vehicle control command to the head unit 20.

The storage 15 stores the driver's private medical information, such as various physical parameters, health problems, IDs, etc., and vehicle control information predetermined to correspond to at least a piece of medical information, which is received from the vehicle control information server 40. The storage 15 also stores the control nodes list received from the head unit 20.

The head unit 20 includes a vehicle controller 21, a transceiver 22, a control node searcher 23, a control node determiner 24, and a storage 25.

The vehicle controller 21 discovers the mobile terminal 10, establishes a connection with the mobile terminal 10, and sends the control nodes list to the mobile terminal 10 through the transceiver 22 at the mobile terminal's request. Upon reception of the vehicle control command via the transceiver 22, the vehicle controller 21 controls operations of at least one vehicle control node 50 according to the received vehicle control command.

Also, upon reception of the driver's private medical information via the transceiver 22, the vehicle controller 21 determines if vehicle control information corresponding to the received driver's private medical information is stored in the storage 25. If the vehicle control information is stored in the storage 25, the vehicle controller 21 controls the control node searcher 23 to search controllable vehicle control nodes in the vehicle. Then, the vehicle controller 21 controls the control node determiner 24 to determine whether there is a piece of vehicle control information for the searched vehicle control node from among the received pieces of vehicle control information, and controls operations of the vehicle control node 50 using the determined vehicle control information.

If no vehicle control information is stored, the vehicle controller 21 sends a request for the vehicle control information predetermined to correspond to at least one piece of driver's private medical information to the vehicle control information server 40 through the transceiver 22. The vehicle controller 21 then sends a request for the vehicle control information to the vehicle control information server 40 through the transceiver 22, and in return, receives the vehicle control information through the transceiver 22. The vehicle controller 21 controls the vehicle control node 50 using the vehicle control information predetermined to correspond to the received private medical information.

The vehicle controller 21, upon reception of a piece of the vehicle control information that corresponds to the control nodes list via the transceiver 22, controls the vehicle control node 50 using the received vehicle control information.

The transceiver 22 forwards the control nodes list of vehicle control nodes to the mobile terminal 10, and receives a vehicle control command from the mobile terminal 10. The transceiver 22 receives the driver's private medical information from the mobile terminal 10, sends a request for vehicle control information to the vehicle control information server 40, and receives the vehicle control information from the vehicle control information server 40. Furthermore, the transceiver 22 receives the vehicle control information from the mobile terminal 10 or the vehicle control information server 40.

The control node searcher 23 searches controllable vehicle control nodes in the vehicle.

The control node determiner 24 determines if there is a piece of vehicle control information for the searched vehicle control node among the received pieces of vehicle control information.

The storage 25 stores the vehicle control information received from the vehicle control information server 40 or the mobile terminal 10, and vehicle control commands received from the mobile terminal 10.

The private medical information server 30 includes a private medical information database 31 in which private medical information for at least one driver is stored. The private medical information includes different medical information, such as physical parameters, health problems, IDs, etc.

The vehicle control information server 40 includes a vehicle control information database 41, in which the vehicle control information is stored, such as commands, allowable parameter values, etc. for controlling different vehicle control nodes, which are predetermined to correspond to the private medical information for the at least one driver.

The vehicle control node 50 includes vehicle nodes to be controllable for driving conditions, such as at least one seat, an air conditioner, mirrors, smart airbags, an engine, etc., all of which are mounted in the vehicle.

As such, the present invention offers the driver optimized driving conditions by automatically controlling a driving condition of the vehicle in response to the driver's private medical information.

In an embodiment of the present invention, either the mobile terminal 10 or the head unit 20 may generate commands to control operations of the vehicle control nodes to offer the optimized vehicle driving condition in response to the driver's private medical information, which will be described below. In the following description of an embodiment of the present invention, it will be assumed that the mobile terminal 10 or the head unit 20 does not have the driver's private medical information and the vehicle control information.

The first case where the mobile terminal 10 generates a command to control the vehicle control node 50 will be described with reference to FIG. 3.

Figure 3:
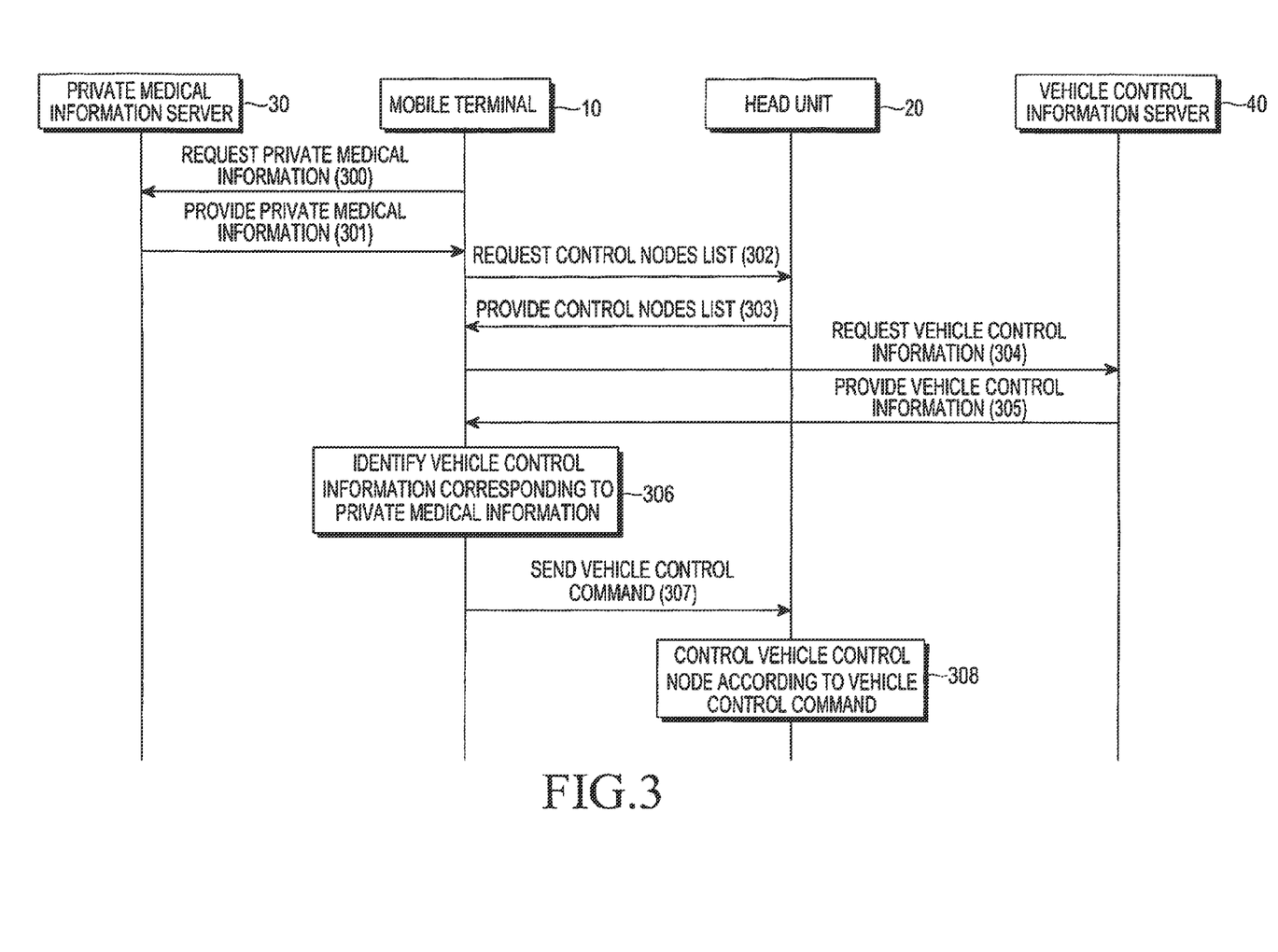
FIG. 3 is a signal flow diagram illustrating a procedure of generating a node control command based on private medical information, a control nodes list, and vehicle control information, which is performed by the mobile terminal, according to an embodiment of the present invention.

FIG. 3 is a signal flow diagram illustrating a procedure of generating a node control command based on the private medical information, the control nodes list, and the vehicle control information, which is performed by the mobile terminal 10, according to an embodiment of the present invention.

In step 300, the mobile terminal 10 sends a request for the driver's private medical information to the private medical information server 30, and in step 301, the private medical information server 30 provides the requested driver's private medical information to the mobile terminal 10.

In step 302, the mobile terminal 10 sends a request for the control nodes list of controllable vehicle control nodes in the vehicle to the head unit 20, and in step 303, the head unit 20 provides the requested control node list to the mobile terminal 10.

In step 304, the mobile terminal 10 sends a request for the vehicle control information to the vehicle control information server 40, and in step 305, the vehicle control information server 40 provides the requested vehicle control information to the mobile terminal 10. In this regard, the vehicle control information server 40 may provide vehicle control information that is predetermined to correspond to the at least a piece of medical information, vehicle control information that corresponds to the requested driver's private medical information, or vehicle control information that corresponds to the control nodes list received from the mobile terminal 10.

In step 306, the mobile terminal 10 identifies pieces of vehicle control information that correspond to the driver's private medical information and the control nodes list from among the received pieces of vehicle control information and generates a vehicle control command to control the vehicle control node according to the identified vehicle control information.

In step 307, the mobile terminal 10 sends the generated vehicle control command to the head unit 20, and in step 308, the head unit 20 controls operations of the vehicle control node according to the received control vehicle command.

In an embodiment of the present invention, messages for request and response among the mobile terminal 10, the head unit 20, the private medical information server 30, and the vehicle control information server 40 may be transmitted/received in a format configured according to the Car Connectivity Consortium (CCC) standard. This will be described in more detail below.

Table 1 shows an example of a request message for the mobile terminal to request the control nodes list of the controllable vehicle control nodes in the vehicle.

TABLE 1

| # Bytes | Type | Value | Description |
|---|---|---|---|
| 2 | U16 | 0*B150 | Message type |
| 2 | U16 | 2 | Payload length |
| 1 | U8 | 1 | CDB (Common Data Bus) sink endpoint major version |
| 1 | U8 | 0 | CDB sink endpoint minor version |

Table 2 shows an example of a response message for the head unit 20 to respond to the request for the control nodes list.

TABLE 2

| # Bytes | Type | Value | Description |
|---|---|---|---|
| 2 | U16 | 0*B150 | Message type |
| 2 | U16 | 2 | Payload length |
| 1 | U8 | 1 | CDB sink endpoint major version |
| 1 | U8 | 0 | CDB sink endpoint minor version |
| 2 | U16 | N | Total number of Control Nodes |
| M | Array of U8 | | Array of Control Nodes as defined in Table 3 |

Table 3 shows an example of a description of the vehicle control node.

TABLE 3

| # Bytes | Type | Value | Description |
|---|---|---|---|
| 2 | U16 | | Unique Service ID |
| 1 | U8 | | Major version of service |
| 1 | U8 | | Minor version of service |
| 2 | U16 | 90 | Minimum angle of Seat Back |
| | | 180 | Maximum angle of Seat Back |
| | | 50 | Min. Distance from Dashboard |
| | | 100 | Max. Distance from Dashboard |
| 2 | U16 | N | Indicates the length of Control Node Name String |
| N | Array of U8 | | Control Node Name String |

Various technologies may be used such that the control node may take control signals transmitted from the head unit 20, such as FlexRay technology for mainly controlling safety related vehicle nodes, such as engines, transmissions, etc., Controller Area Network (CAN) or Local Interconnect Network (LIN) technology for controlling convenience related nodes like car seats, and Media Oriented Systems Transport (MOST) technology for exchanging multimedia entertainment content, such as audio and videos.

Next, the case where the head unit 20 generates a command to control the vehicle control node 50 will be described with reference to FIGS. 4 to 6.

The manner in which the head unit 20 controls operations of the vehicle control node may prevent a third party with malicious intent from controlling the vehicle.

Figure 4:
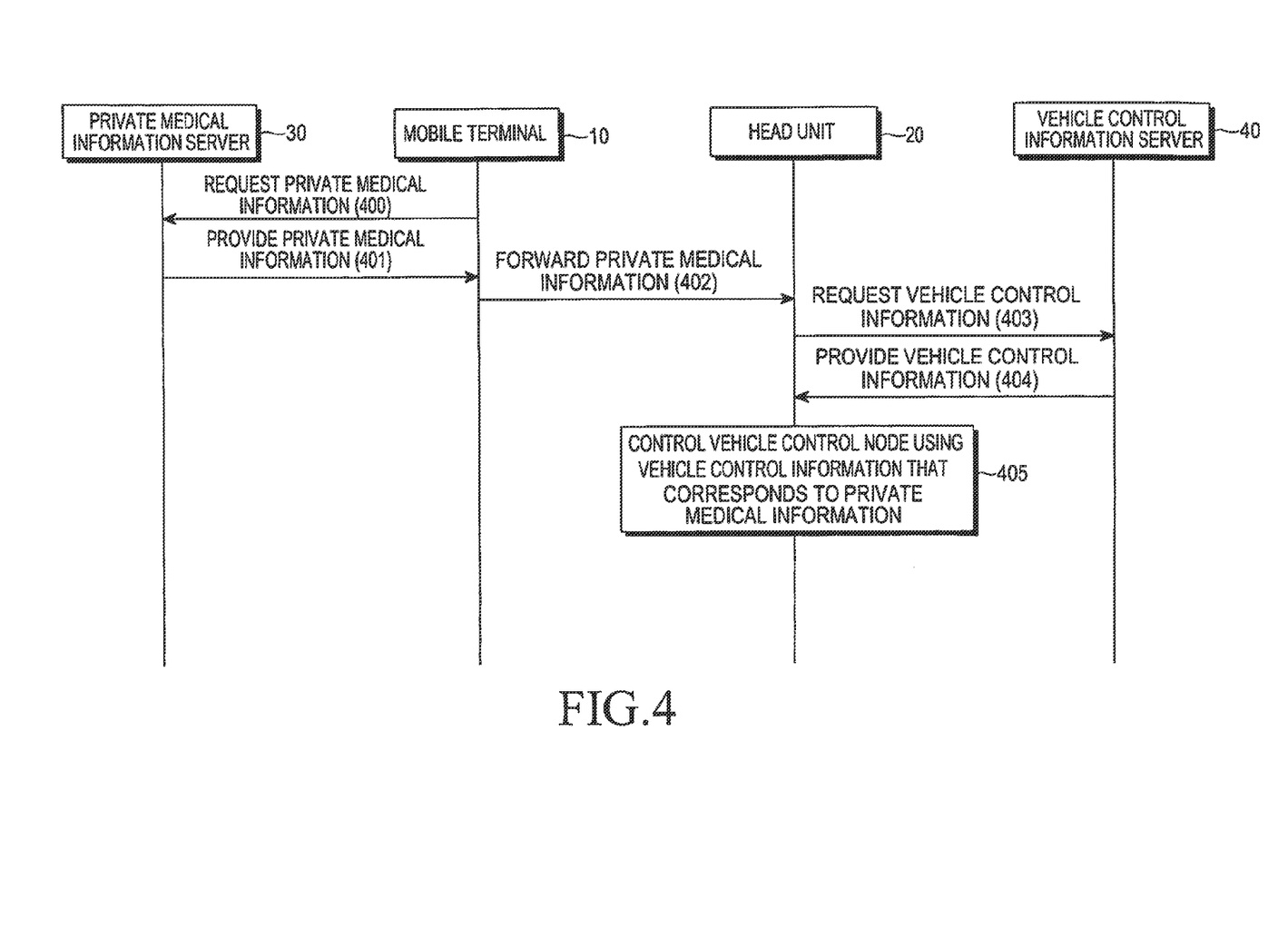
FIG. 4 is a signal flow diagram illustrating a procedure of controlling a vehicle control node by obtaining driver's private medical information and vehicle control information, which is performed by the head unit, according to an embodiment of the present invention.

FIG. 4 is a signal flow diagram illustrating a procedure of controlling the vehicle control node 50 by obtaining the driver's private medical information and vehicle control information, which is performed by the head unit 20, according to an embodiment of the present invention.

In step 400, the mobile terminal 10 sends a request for the driver's private medical information to the private medical information server 30, and in step 401, the private medical information server 30 provides the requested private medical information to the mobile terminal 10.

In step 402, the mobile terminal 10 forwards the received private medical information to the head unit 20, and in step 403, the head unit 20 sends a request for the vehicle control information to the vehicle control information server 40. In step 404, the vehicle control information server 40 provides the requested vehicle control information to the head unit 20, the vehicle control information being predetermined to correspond to at least one driver.

In step 405, the head unit 20 identifies a piece of vehicle control information that corresponds to the driver's private medical information from among the received pieces of vehicle control information, and controls the vehicle control node 50 using the identified vehicle control information. In other words, the head unit 20 generates a command to control the vehicle control node 50 using the identified vehicle control information, and controls operations of the vehicle control node 50 according to the command.

Figure 5:
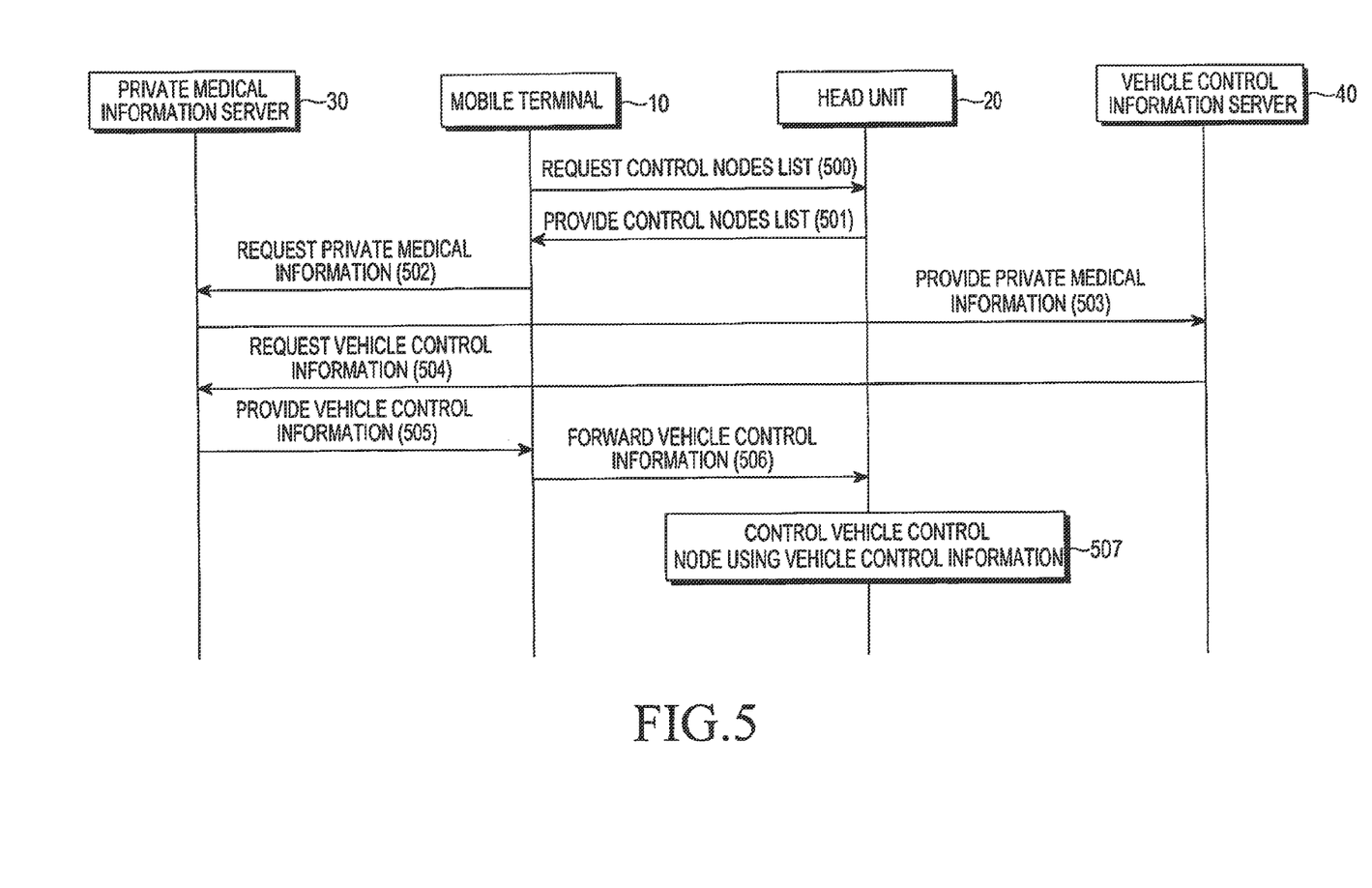
FIGS. 5 and 6 are signal flow diagrams illustrating procedures of controlling the vehicle control node using vehicle control information provided by the vehicle control information server, that corresponds to the driver's private medical information, which is performed by the head unit, according to an embodiment of the present invention.
Figure 6:
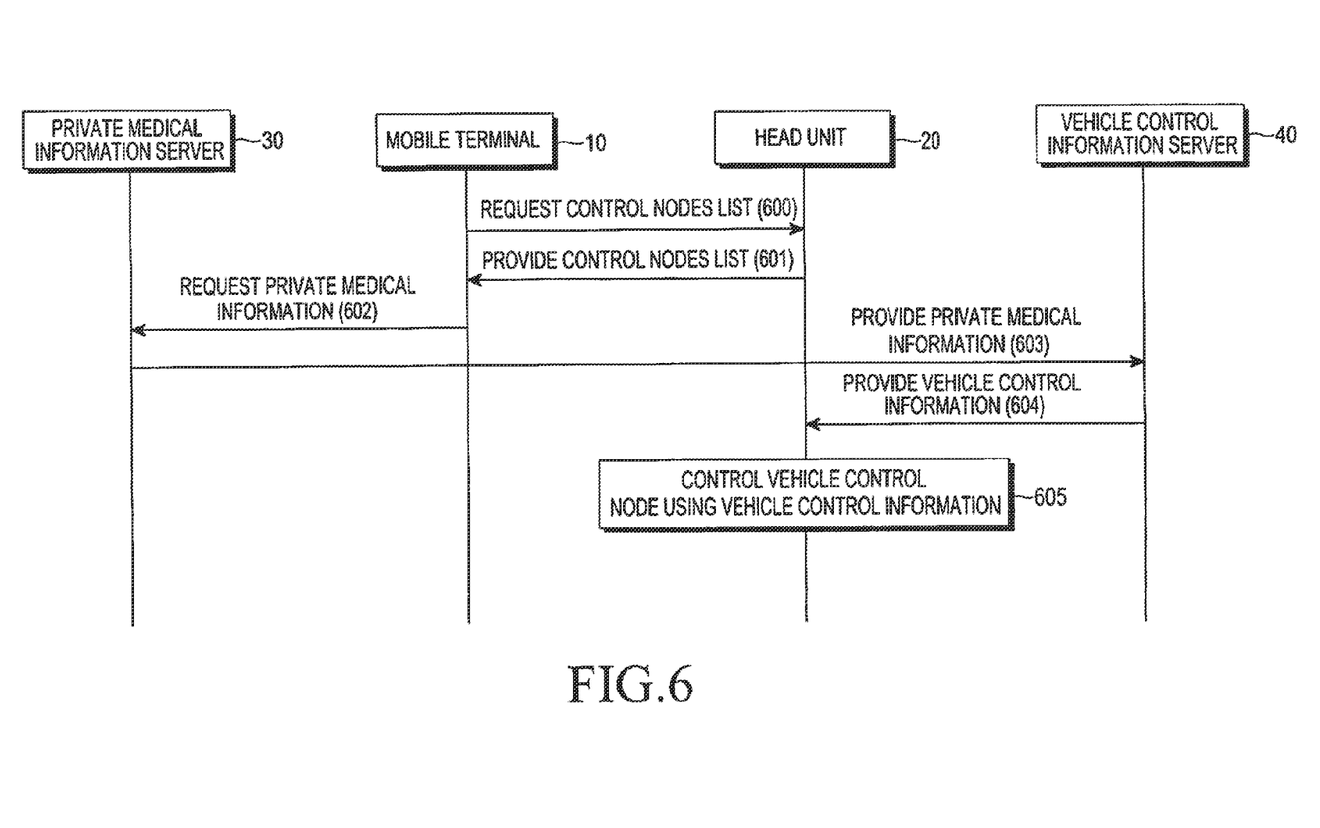

FIGS. 5 and 6 are signal flow diagrams illustrating procedures of the head unit 20 controlling the vehicle control node 50 using vehicle control information in response to the driver's private medical information, provided by the vehicle control information server 40, according to an embodiment of the present invention.

In FIG. 5, the signal flow diagram illustrates that the vehicle control information server 40, upon reception of the driver's private medical information from the private medical information server 30, provides vehicle control information in response to the received driver's private medical information to the head unit 20 via the private medical information server 30 and the mobile terminal 10. In FIG. 6, the signal flow diagram illustrates that the vehicle control information server 40, upon reception of the driver's private medical information from the private medical information server 30, provides vehicle control information in response to the received driver's private medical information directly to the head unit 20.

In step 500 of FIG. 5, the mobile terminal 10 sends a request for the control nodes list of vehicle control nodes controllable for a driving condition to the head unit 20, and in step 501, the head unit 20 provides the requested control node list to the mobile terminal 10.

In step 502, the mobile terminal 10 sends a request for the driver's private medical information to the private medical information server 30, and in step 503, the private medical information server 30 provides the requested driver's private medical information to the vehicle control information server 40.

In step 504, the vehicle control information 40 detects a piece of vehicle control information among pieces of vehicle control information stored in the vehicle control information database 41 that corresponds to the received driver's private medical information, and provides the detected vehicle control information to the private medical information server 30.

In step 505, the private medical information server 30 provides the received vehicle control information to the mobile terminal 10, and in step 506, the mobile terminal 10 forwards the received vehicle control information to the head unit 20.

In step 507, the head unit 20 controls operations of the vehicle control node using the received vehicle control information. In other words, the head unit 20 generates a command to control the vehicle control node 50 using the received vehicle control information, and controls operations of the vehicle control node 50 according to the command.

Referring to FIG. 6, in step 600, the mobile terminal 10 sends a request for the control nodes list of controllable vehicle control nodes in the vehicle to the head unit 20, and in step 601, the head unit 20 provides the requested control node list to the mobile terminal 10.

In step 602, the mobile terminal 10 sends a request for the driver's private medical information to the private medical information server 30, and in step 603, the private medical information server 30 provides the requested driver's private medical information to the vehicle control information server 40.

In step 604, the vehicle control information server 40 provides the vehicle control information that corresponds to the received driver's private medical information directly to the head unit 20, and in step 605, the head unit 20 controls operations of the vehicle control node 50 using the received vehicle control information. As such, according to the above method, the head unit 20 may control operations of the vehicle control node 50 safely since the vehicle control information in response to the driver's private medical information is identified and provided by the vehicle control information server 40 instead of the mobile terminal 10 and the head unit 20.

Furthermore, in the embodiment of the present invention, the vehicle control information server 40 provides the head unit 20 with at least a piece of vehicle control information predetermined to correspond to at least a piece of the medical information, and the head unit 20 detects a piece of vehicle control information that corresponds to the driver's private medical information, generates a vehicle control command in response to the detected vehicle control information, and controls the vehicle control node 50 according to the vehicle control command.

As such, the present invention offers the driver optimized driving conditions by automatically controlling a driving condition of the vehicle in response to the driver's private medical information.

Figure 7:
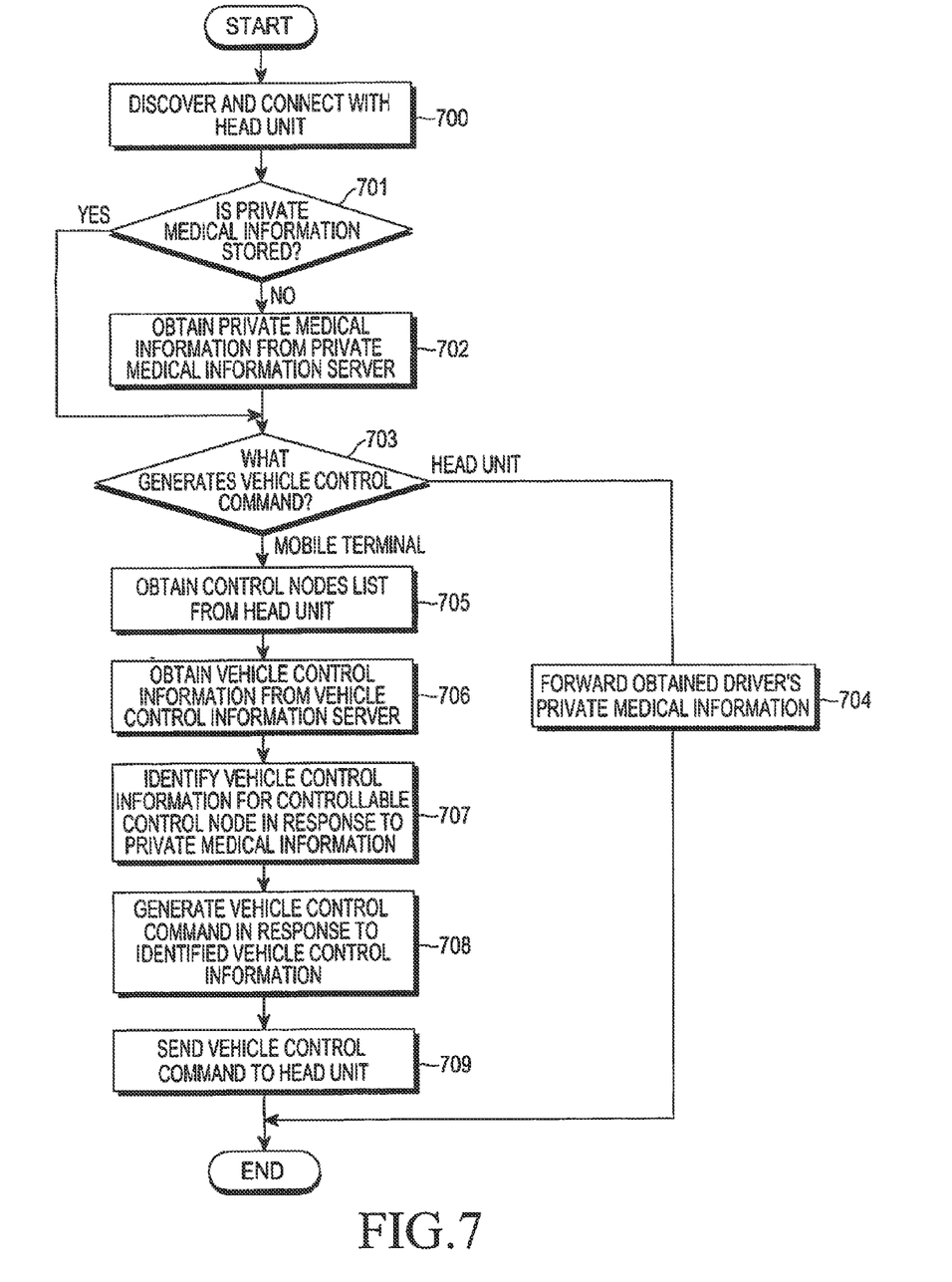
FIG. 7 is a flowchart illustrating a procedure of controlling the vehicle for a driving condition, which is performed by the mobile terminal, according to an embodiment of the present invention.

FIG. 7 is a flowchart illustrating a procedure of controlling the vehicle for a driving condition, which is performed by the mobile terminal, according to an embodiment of the present invention.

In step 700, the terminal controller 11 discovers the head unit 20 and establishes a connection with the head unit 20.

In step 701, the terminal controller 11 determines if the driver's private medical information is stored in the storage 15, and if so, proceeds to step 703, or else, proceeds to step 702 in which the driver's private medical information is obtained from the private medical information server 30.

In step 703, if the mobile terminal 10 generates the vehicle control command, the terminal controller 11 proceeds to step 705, or otherwise, if the head unit 20 generates the vehicle control command, the terminal controller 11 proceeds to step 704 in which to forward the obtained driver's private medical information to the head unit 20, and then the process ends.

The terminal controller 11 obtains the control nodes list from the head unit 20, in step 705, and obtains the vehicle control information predetermined to correspond to at least one piece of medical information from the vehicle control information server, in step 706.

The terminal controller 11 identifies a piece of vehicle control information for the vehicle control node controllable in response to the driver's private medical information, in step 707, and generates a vehicle control command according to the identified vehicle control information, in step 708.

In step 709, the terminal controller 11 sends the vehicle control command for the head unit 20 to control operations of the vehicle control node, and then stops the procedure of controlling the vehicle.

Figure 8:
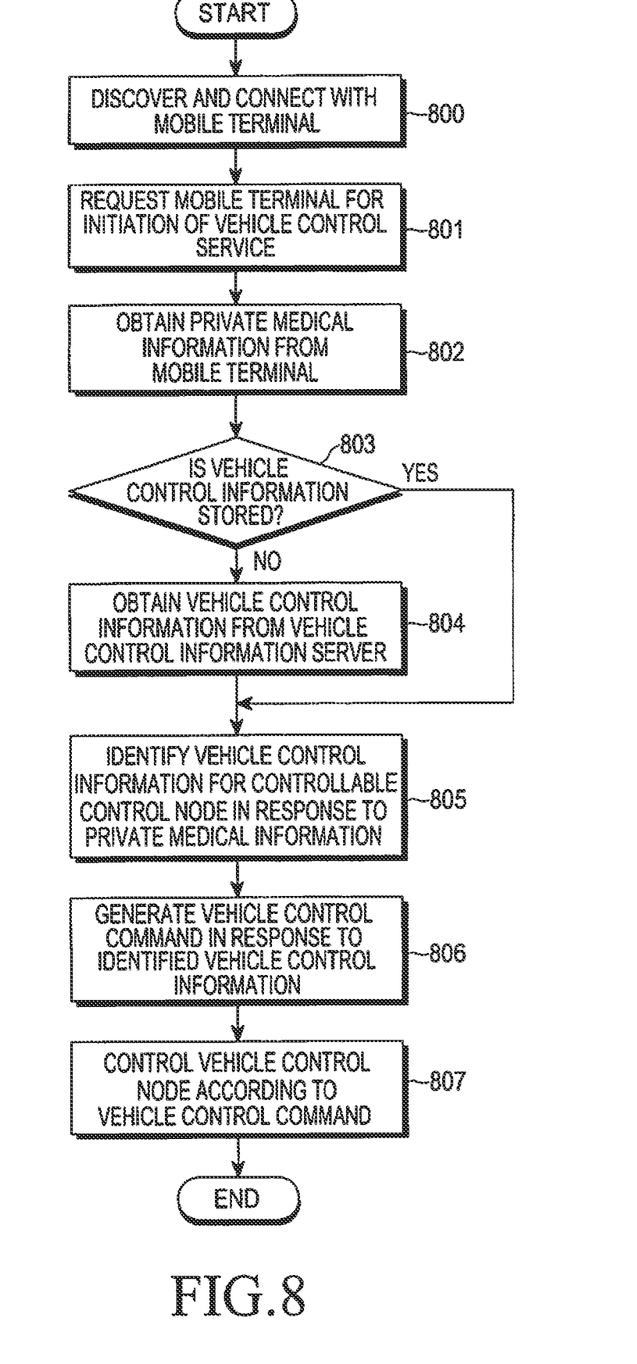
FIG. 8 is a flowchart illustrating a procedure of controlling the vehicle for a driving condition, which is performed by the head unit, according to an embodiment of the present invention.

FIG. 8 is a flowchart illustrating a procedure of controlling the vehicle for a driving condition, which is performed by the head unit 20, according to an embodiment of the present invention.

The vehicle controller 21 discovers the mobile terminal 10 and establishes a connection with the mobile terminal 10, in step 800, and sends a request for initiation of a vehicle control service to the mobile terminal 10, in step 801.

In step 802, the vehicle controller 21 requests and obtains the private medical information from the mobile terminal 10.

In step 803, the vehicle controller 21 determines if the vehicle control information is stored in the storage 25, and if so, proceeds to step 805, or else, proceeds to step 804 in which the vehicle control information is obtained from the vehicle control information server 40. In other words, the vehicle controller 21 controls the control node searcher 23 to search the controllable vehicle control node, and controls the control node determiner 24 to determine if there is a piece of vehicle control information for the searched vehicle control node among the received pieces of vehicle control information. The obtained vehicle control information is determined in advance to correspond to at least a piece of medical information.

In step 805, the vehicle controller 21 identifies from the obtained pieces of vehicle control information a piece for the vehicle control node controllable in response to the private medical information.

The vehicle controller 21 generates the vehicle control command according to the identified vehicle control information, in step 806, and controls operations of the vehicle control node 50 according to the vehicle control command, in step 807.

As such, the present invention offers the driver optimized driving conditions by automatically controlling a driving condition of the vehicle in response to the driver's private medical information.

Figure 9:
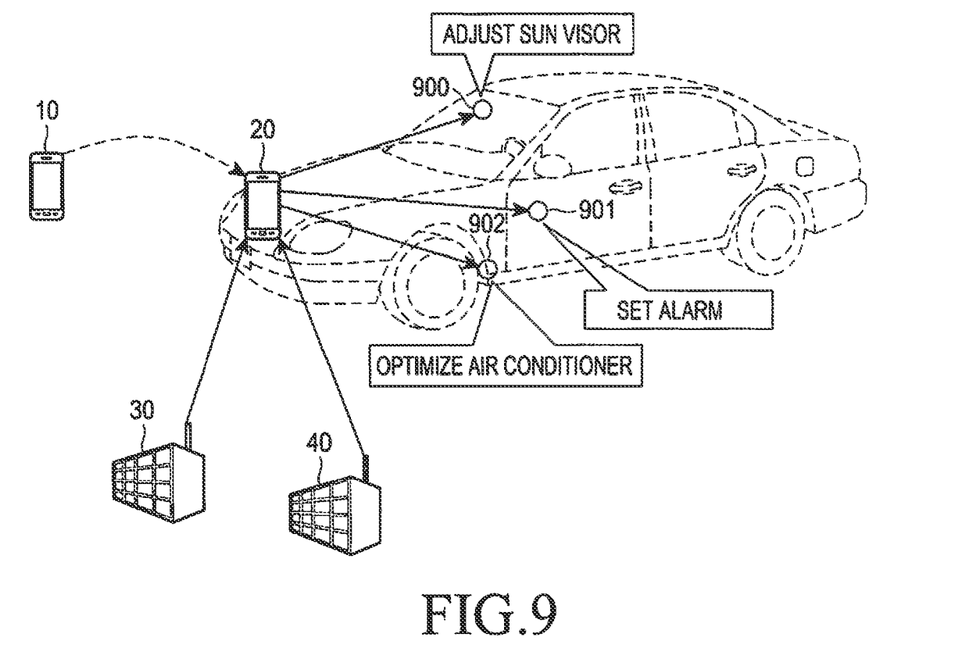
FIGS. 9 and 10 illustrate diagrams procedures of controlling driving conditions of the vehicle based on the driver's private medical information.
Figure 10:
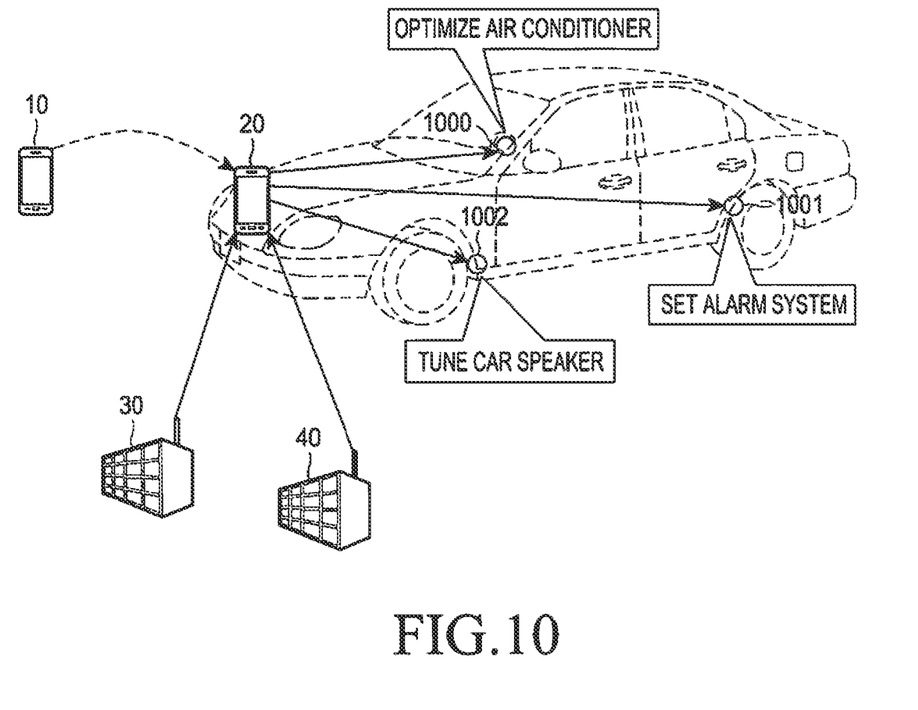

FIGS. 9 and 10 illustrate diagrams of procedures of controlling driving conditions of the vehicle in response to the driver's private medical information.

Referring to FIGS. 9 and 10, when a driver gets in the vehicle with his/her mobile terminal 10, the driver's private medical information, such as the driver's medical history or health problems is transferred from the mobile terminal 10 to the head unit 20 of the vehicle. The driver's private medical information may be stored in the driver's mobile terminal 10 in advance, or may be received from the private medical information server 30. The head unit 20 controls vehicle control nodes using vehicle control information for a driving condition for the vehicle in response to the driver's private medical information. The vehicle control information may be stored in the head unit 20 in advance, or received from the vehicle control information server 40.

In this regard, assuming that the driver suffers from chronic diabetes and carries around insulin, the head unit 20 may control the vehicle driving condition according to the vehicle control information predetermined for a diabetes patient as follows:

First, since insulin deteriorates when exposed to high temperatures over a long period of time, the head unit 20 may control an air conditioner 902 to automatically keep the indoor temperature of the vehicle at a proper level to prevent the insulin deterioration. Further, the head unit 20 may control the air direction of the air conditioner 902 toward the driver's feet in case the diabetes causes poor foot health as a side effect. In addition, since direct sunlight and reflected light may easily hurt the driver's eyes, the head unit 20 may control a sun visor 900 in front of the driver's seat to be automatically adjusted to efficiently prevent direct sunlight. Furthermore, the head unit 20 may set an alarm 901 for the driver to periodically intake sugar in order to prevent a sudden drop of his/her blood sugar level.

Referring to FIG. 10, assuming that the driver suffers from tympanitis in his/her right ear and cannot hear well with the right ear, the head unit 20 may control the vehicle driving condition according to the vehicle control information predetermined for a tympanitis patient as follows:

The head unit 20 may control an air conditioner 1000 to automatically adjust the indoor temperature and humidity of the vehicle in order not to worsen the driver's tympanitis, and control a car speaker 1002 to adjust the sound balance in order for the driver who hears with only one ear not to feel inconvenience in listening to music or GPS voice. In addition, the head unit 20 may control to replace a warning sound or alarm 1001 from a rear warning sensor used for rear parking by a warning display on a screen of the vehicle.

As such, the present invention offers the driver optimized driving conditions by automatically controlling a driving condition of the vehicle in response to the driver's private medical information.

While the present invention has been particularly shown and described with reference to certain embodiments thereof, it will be understood by those of ordinary skill in the art that various changes in form and details may be made therein without departing from the spirit and scope of the present invention as defined by the following claims.

What is claimed is:

1. A vehicle control apparatus using a driver's medical information, the apparatus comprising:
   a transceiver configure to transmit/receive vehicle information used to control a vehicle; and
   a vehicle controller configure to:
   search vehicle control nodes to be controlled in the vehicle upon reception of the driver's medical information from a medical information server;
   select at least one vehicle control node that corresponds to the driver's medical information from among the searched vehicle control nodes;
   identify vehicle control information for controlling the selected at least one vehicle control node from among vehicle control information received from a vehicle control information server; and
   control the selected at least one vehicle control node using the identified vehicle control information.

2. The vehicle control apparatus of claim 1, wherein the vehicle controller obtains the vehicle control information from the vehicle control information server having pieces of vehicle control information predetermined to correspond to at least a piece of medical information, if there is no vehicle control information for controlling the searched vehicle control node.

3. The vehicle control apparatus of claim 1, wherein the vehicle controller, at a request of a mobile terminal for a control nodes list of the vehicle control nodes, transfers the requested control nodes list to the mobile terminal via the transceiver.

4. The vehicle control apparatus of claim 1, wherein the vehicle controller, upon reception of a vehicle control command in response to the vehicle control information via the transceiver, controls the searched vehicle control node according to the received vehicle control command.

5. A mobile terminal for controlling a vehicle using a driver's medical information, the mobile terminal comprising:
- a transceiver configure to transmit/receive information used to control a vehicle;
- a terminal controller configure to:
  - obtain the driver's medical information for adjustment of a driving condition from a medical information server having the driver's medical information;
  - obtain a control nodes list of controllable vehicle control nodes in the vehicle from a head unit of the vehicle;
  - obtain vehicle control information predetermined to correspond to at least one piece of medical information from a vehicle control information server;
  - generate a vehicle control command to control the vehicle control nodes according to the vehicle control information in response to the obtained driver's medical information; and
  - send the generated vehicle control command to the head unit.

6. The mobile terminal of claim 5, wherein the terminal controller identifies vehicle control information for the obtained control nodes list in response to the obtained driver's medical information.

7. The mobile terminal of claim 5, wherein the terminal controller forwards the driver's medical information obtained from the medical information server to the head unit.

8. The mobile terminal of claim 5, wherein the terminal controller obtains the control nodes list from the head unit; sends a request for the driver's medical information to the medical information server; receives the vehicle control information that corresponds to the driver's medical information from the medical information server; and forwards the vehicle control information to the head unit.

9. A vehicle control method using a driver's medical information, the method comprising:
- searching, by a vehicle controller, vehicle control nodes to be controlled in a vehicle upon reception of the driver's medical information from a medical information server;
- selecting, by the vehicle controller, at least one vehicle control node that corresponds to the driver's medical information from among the searched vehicle control nodes;
- identifying vehicle control information for controlling the selected at least one vehicle control node from among vehicle control information received from a vehicle control information server; and
- controlling, by the vehicle controller, the selected at least one vehicle control node using the identified vehicle control information.

10. The vehicle control method of claim 9, further comprising:
- obtaining, by the vehicle controller, the vehicle control information from the vehicle control information server having pieces of vehicle control information predetermined to correspond to at least a piece of medical information, if there is no vehicle control information for controlling the searched vehicle control node.

11. The vehicle control method of claim 9, further comprising:
- transferring, by the vehicle controller, at a request of a mobile terminal for a control nodes list of the vehicle control nodes in the vehicle, the requested control nodes list to the mobile terminal.

12. The vehicle control method of claim 9, further comprising:
- controlling, by the vehicle controller, upon reception of the vehicle control information that corresponds to the driver's medical information, the searched vehicle control node using the received vehicle control information.

13. The vehicle control method of claim 9, further comprising: controlling, by the vehicle controller, upon reception of a vehicle control command in response to the vehicle control information, the searched vehicle control node according to the received vehicle control command.

14. A method of controlling a vehicle using a driver's medical information in a mobile terminal, the method comprising:
- obtaining, by a terminal controller, the driver's medical information for adjustment of a driving condition from a medical information server having the driver's medical information;
- obtaining, by the terminal controller, a control nodes list of controllable vehicle control nodes in the vehicle from a head unit of the vehicle;
- obtaining, by the terminal controller, vehicle control information predetermined to correspond to at least one piece of medical information from a vehicle control information server;
- generating, by the terminal controller, a vehicle control command to control the vehicle control nodes according to the vehicle control information in response to the obtained driver's medical information; and
- sending, by the terminal controller, the generated vehicle control command to the head unit.

15. The method of claim 14, wherein controlling the vehicle control nodes comprises,
- identifying, by the terminal controller, the vehicle control information for the obtained control nodes list in response to the obtained driver's medical information.

16. The method of claim 14, further comprising:
- forwarding, by the terminal controller, the driver's medical information obtained from the medical information server to the head unit.

17. The method of claim 14, further comprising:
- obtaining, by the terminal controller, the control nodes list from the head unit, sending a request for the driver's medical information to the medical information server, and receiving the vehicle control information that corresponds to the driver's medical information from the medical information server; and forwarding the received vehicle control information to the head unit.

\* \* \* \* \*